US012582372B2

(12) United States Patent
 Giers et al.

(10) Patent No.: US 12,582,372 B2
(45) Date of Patent: Mar. 24, 2026

(54) APPARATUS AND CORRESPONDING METHOD FOR MEASURING LUMBAR SPINE

(71) Applicant: Oregon State University, Corvallis, OR (US)

(72) Inventors: Morgan B. Giers, Corvallis, OR (US); Sonia Ahrens, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 264 days.

(21) Appl. No.: 18/296,941

(22) Filed: Apr. 6, 2023

(65) Prior Publication Data

US 2023/0320683 A1 Oct. 12, 2023

Related U.S. Application Data

(60) Provisional application No. 63/362,659, filed on Apr. 7, 2022.

(51) Int. Cl.
| | |
|---|---|
| *G06T 7/70* | (2017.01) |
| *A61B 6/00* | (2006.01) |
| *A61B 6/50* | (2024.01) |
| *G06T 3/60* | (2006.01) |
| *G06T 7/00* | (2017.01) |
| *G06T 7/11* | (2017.01) |
| *G06T 7/13* | (2017.01) |
| *G06T 7/62* | (2017.01) |
| *G06T 7/66* | (2017.01) |

(52) U.S. Cl.
 CPC ............ *A61B 6/5217* (2013.01); *A61B 6/505* (2013.01); *G06T 3/60* (2013.01); *G06T 7/0012* (2013.01); *G06T 7/11* (2017.01); *G06T 7/13* (2017.01); *G06T 7/62* (2017.01); *G06T 7/66* (2017.01); *G06T 7/70* (2017.01); *G06T 2207/10081* (2013.01); *G06T 2207/10088* (2013.01); *G06T 2207/10116* (2013.01); *G06T 2207/30012* (2013.01)

(58) Field of Classification Search
 CPC ......... A61B 6/5217; A61B 6/505; G06T 3/60; G06T 7/0012; G06T 7/11; G06T 7/13; G06T 7/62; G06T 7/66; G06T 7/70; G06T 2207/10081; G06T 2207/10088; G06T 2207/10116; G06T 2207/30012
 USPC ......................................................... 382/128
 See application file for complete search history.

(56) References Cited

U.S. PATENT DOCUMENTS

2007/0127799 A1* 6/2007 Reisman ................. G06T 7/136
382/128

OTHER PUBLICATIONS

Abdu et al., "Reoperation for Recurrent Intervertebral Disc Herniation in the Spine Patient Outcomes Research Trial: Analysis of Rate, Risk Factors and Outcomes," Spine (Phila Pa 1976), Jul. 15, 2017 vol. 42, No. 14:1106-1114. doi: 10.1097/BRS.0000000000002088 (16 pages).

(Continued)

*Primary Examiner* — Stephen P Coleman
(74) *Attorney, Agent, or Firm* — MUGHAL GAUDRY & FRANKLIN PC

(57) ABSTRACT

Described herein is a technique (e.g., apparatus and method) to improve consistency of lumbar lordosis (LL) and disc height index (DHI) measurements. In at least one embodiment, one or more processors are to measure lumber spine based, at least in part, on cross-sectional area and optical center of mass of segmented intervertebral discs (IVDs).

9 Claims, 13 Drawing Sheets

(56)                    References Cited

OTHER PUBLICATIONS

Belykh et al., "Preoperative Estimation of Disc Herniation Recurrence After Microdiscectomy: Predictive Value of a Multivariate Model Based on Radiographic Parameters," The Spine Journal vol. 17, 2017, pp. 390-400 (11 pages).

Deyo et al., "Opioids for Low Back Pain," British Medical Journal, vol. 350, Jan. 5-11, 2015, https://www.jstor.org/stable/26517792, doi: 10.1136, pp. 1-13 (14 pages).

Deyo et al., "Trends and Variations in the Use of Spine Surgery," Clinical Orthopaedics and Related Research a Publication of the Association of Bone and Joint Surgeons, Section I: Symposium II: Surgical Versus Nonsurgical Management of Spinal Disorders, vol. 443, Feb. 2006, https://journals.lww.com/clinorthop/Fulltext/2006/02000/Trends_and_Variations_in_the_Use_of_Spine_Surgery.23.aspx, DOI: 10.1097/01.blo.0000198726.62514.75, pp. 139-146 (7 pages).

Hedlund et al., "The Long-Term Outcome of Lumbar Fusion in the Swedish Lumbar Spine Study," The Spine Journal, vol. 16 Issue 5, Sep. 9, 2015, https://www.thespinejournalonline.com/article/S1529-9430(15)01371-6/fulltext, pp. 579-587 (8 Pages).

Hegman et al., "Invasive Treatments for Low Back Disorders," in Journal of Occupational and Environmental Medicine, vol. 63, No. 4, Apr. 2021, pp. e215-e241 (27 pages).

Inoue et al., "Radiographic Evaluation of the Lumbosacral Disc Height," Skeletal Radiology, vol. 28, Nov. 1999, https://doi.org/10.1007/s002560050566, pp. 638-643 (6 pages).

Kim, "Disc Height and Segmental Motion as Risk Factors for Recurrent Lumbar Disc Herniation," in Spine, vol. 34, Issue 24, 2009 pp. 2674-2678 (7 pages).

Kyoung-Tae et al., "Disc Height and Segmental Motion as Risk Factors for Recurrent Lumbar Dis Herniation," The Spine Journal, vol. 34 Issue 24, Nov. 15, 2009, https://archive.org/details/sim_spine-us_2009-11-15_34_24, pp. 2674-2678 (4 pages).

Langensiepen et al., "Measuring Procedures to Determine the Cobb Angle in Idiopathic Scoliosis: a Systematic Review," Eur Spine Journal, vol. 22, 2013, DOI 10.1007/s00586-013-2693-9, pp. 2360-2371 (12 pages).

Licina et al., "Section 18, Chapter 2: Recurrent Disc Herniation—Diagnosis and Management," International Society for the Study of the Lumbar Spine, Year, pp. 1-22 (22 pages).

Mannion et al., "Consensus at Last! Long-Term Results of all Randomized Controlled Trials Show That Fusion is No Better Than Non-Operative Care in Improving Pain and Disability in Chronic Low Back Pain," The Spine Journal, vol. 16 Issue 5, 2016, pp. 588-590 (4 pages).

Shaheed et al., "Efficacy, Tolerability, and Dose-Dependent Effects of Opioid Analgesics for Low Back Pain: A Systematic Review and Meta-Analysis," JAMA Internal Medicine, vol. 176 Issue 7, May 23, 2016, doi:10.1001/jamainternmed.2016.1251, pp. 958-968 (11 pages).

Singh et al., "Spine Procedures," The Burden of Musculoskeletal Diseases in the United States 4th Edition, 2014, Spine Disorders, Low Back and Neck Pain, Spine Procedures, https://www.boneandjointburden.org/print/book/export/html/1065, (10 pages).

Wang et al., "A Meta-Analysis of Interlaminar Minimally Invasive Discectomy Compared to Conventional Microdiscectomy for Lumbar Disk Herniation," Clinical Neurology and Neurosurgery, vol. 127, 2014, https://doi.org/10.1016/j.clineuro.2014.10.001, pp. 149-157 (9 pages).

Weinstein et al., "United States Trends and Regional Variations in Lumbar Spine Surgery: 1992-2003," Spine (Phila Pa 1976), vol. 31 Issue 23, Nov. 1, 2006, DOI: 10.1097/01.brs.0000248132.15231.fe, pp. 2707-2714 (19 Pages).

Zahrai et al., "Surgeon Clinical Practice Variation and Patient Preferences During the Informed Consent Discussion: A Mixed-Methods Analysis in Lumbar Spine Surgery," Can J Surg, vol. 63 Issue 3, May 21, 2020, doi: 10.1503/cjs.005619, pp. E284-E291 (8 pages).

* cited by examiner

Disc Height Index (DHI) Calculation

400

Obtain image
401

Obtain segmented IVD masks
402

Calculate disk height index (DHI)
403

Calculate lumber Lordosis (LL)
404

Show calculations
405

Perform Radiography
501

Transfer to server
502

Transfer to memory
503

500
(e.g., 401)

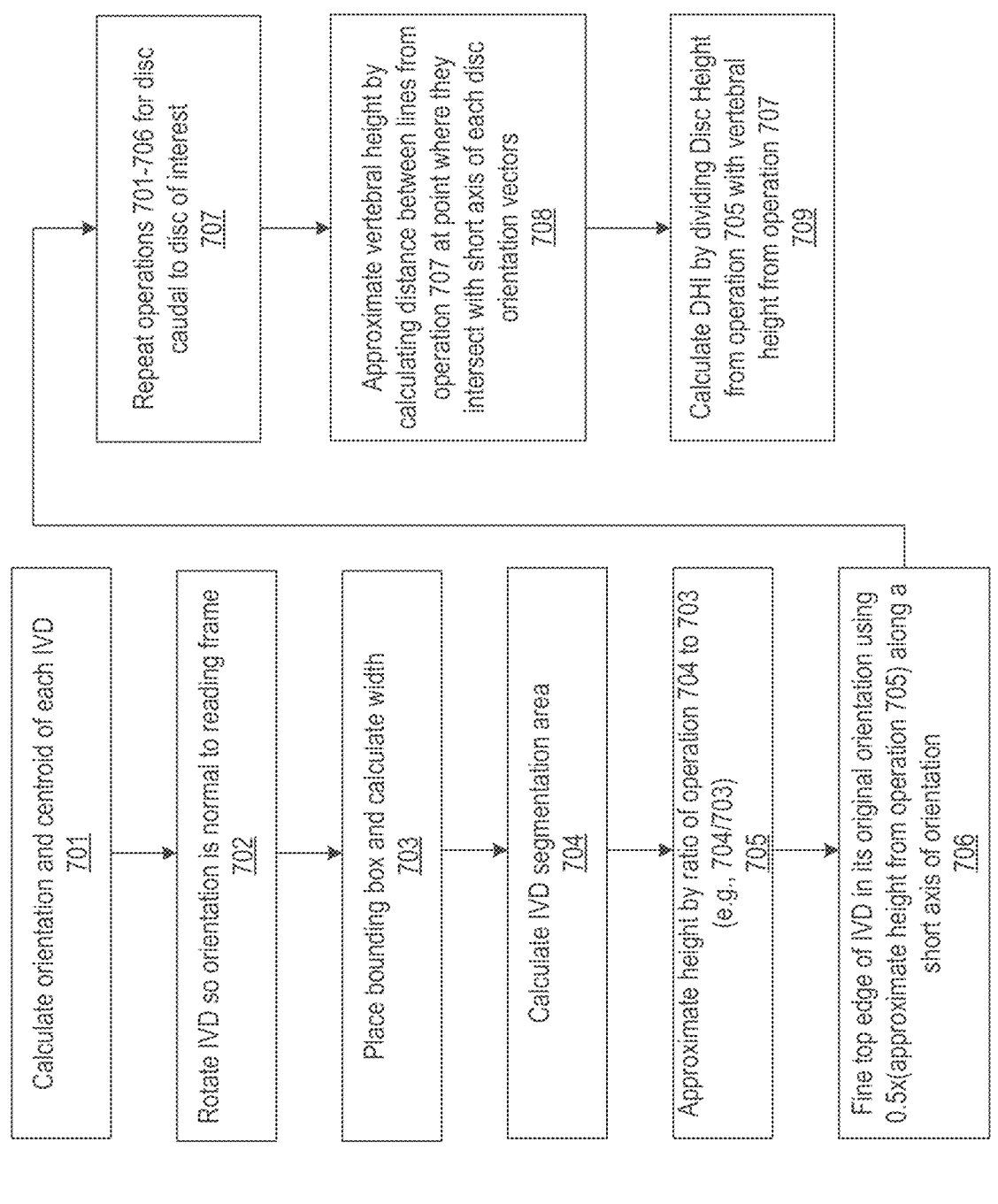

700
(e.g., 404)

Calculate orientation and centroid of each IVD
701

Rotate IVD so orientation is normal to reading frame
702

Place bounding box and calculate width
703

Calculate IVD segmentation area
704

Approximate height by ratio of operation 704 to 703
(e.g., 704/703)
705

Fine top edge of IVD in its original orientation using 0.5x(approximate height from operation 705) along a short axis of orientation
706

Repeat operations 701-706 for disc caudal to disc of interest
707

Approximate vertebral height by calculating distance between lines from operation 707 at point where they intersect with short axis of each disc orientation vectors
708

Calculate DHI by dividing Disc Height from operation 705 with vertebral height from operation 707
709

Fig. 7

Find centroid and orientation of disc T12/L1
801

Find centroid and orientation of disc L5/S1
802

Find angle of intersection points of two orientation vector long axes
803

800
(e.g., 405)

Save the DHI and LL calculation to server
901

Print DHI and LL calculations and image with line placements to computer monitor
902

Evaluate calculations and line placements
903

900
(e.g., 406)

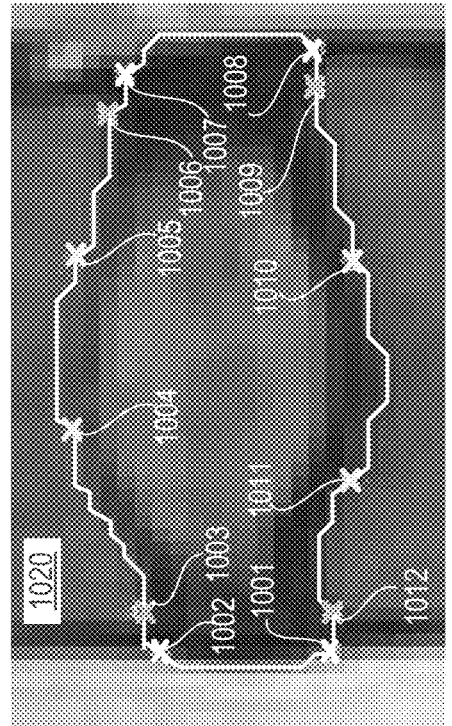
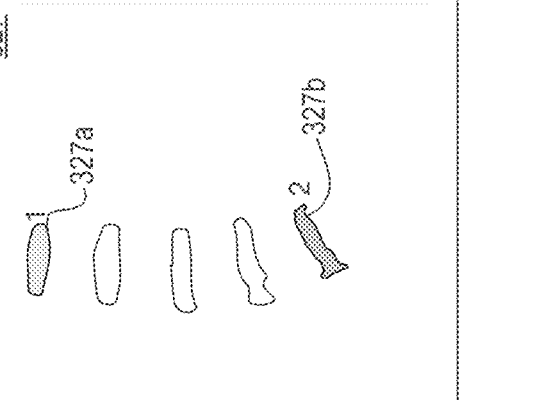
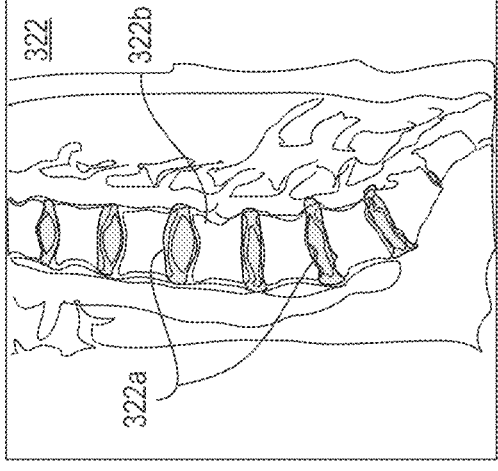
Fig. 10

APPARATUS AND CORRESPONDING METHOD FOR MEASURING LUMBAR SPINE

CLAIM OF PRIORITY

This application claims priority to U.S. Provisional Patent Application 63/362,659 filed Apr. 7, 2022, titled "Apparatus and Corresponding Method for Measuring Lumbar Spine," which is incorporated in its entirety herein.

TECHNICAL FIELD

This application relates to computer related apparatus and methods for measuring lumbar spine. In at least one embodiment, lumber spine is measured based, at least in part, on cross-sectional area and object center of mass of segmented intervertebral discs from a medical image (IVDs).

BACKGROUND

There are more than 1.3 million spine surgeries nationally per year. Among these, the most common procedures are spinal fusions (34%), discectomies (25%), and insertion of devices like artificial discs (22%). Many times, there are multiple surgical options that can be considered. It is a surgeon and patient's "best guess" as to which surgery will be most successful. Choice of surgery is strongly influenced by a surgeon's training and procedure they are most comfortable with. A surgeon will generally recommend a certain surgery to a patient who may decide if they want the procedure or not. Although there are often several options for type of surgery to be performed, the patient is usually unaware of other surgical options. There is currently no tool for providing an objective evaluation for likelihood of success of various types of surgeries. Many risk factors have been independently identified, but their individual and combined contributions to complication risk and outcome success have not been determined. Overall, success of spine operations reducing patients pain long term leaves a lot to be desired. Fusions have reoperation rates of 26-35% and are prone to prolonged complications such as enduring pain and disability. Artificial discs suffer from a limited lifespan of around 15 years. An average patient receives spine surgery in their early 40s and would need to have one or more devices replaced, possibly several times, within their lifespan. 5-10% of discectomy patients re-herniate within a year and many more will convert to a fusion surgery within a decade. There are many efforts to standardize procedure selection process, but one major barrier is lack of repeatability of radiographic evaluations between institutions. Various measurements of spine curvature and degeneration are very subjective to the individual performing the measurement. Meanwhile, back pain patients suffer from continuing pain, disability, and poor quality of life while undergoing repeated operations that often fail to help. For a patient there are many lost workdays, a high potential for opioid dependency, and money paid out of pocket. For hospitals and payers there are millions spent in reoperation costs when complications occur.

Historically, patient images are evaluated for the Disc Height Index (DHI) using manual methods. Manual measurement of DHI via Kim's method is typically performed on radiographs ("X-rays") or Magnetic Resonance (MR) images. For the manual measurement, centers of vertebral bodies adjacent to a disc are first identified. In this case, a center is defined as an intersection of two diagonal lines drawn between opposite corners of a vertebral body. Thereafter, a mid-sagittal line is drawn, connecting centers of adjacent vertebra. The Mid-sagittal line is then used to calculate DHI, which is defined as a height of a disc divided by a height of a vertebral body above it.

Lumbar Lordosis (LL) is typically calculated using Cobb's method which is performed on radiographs (e.g., X-rays) or MR images. There are four lines used to calculate a Cobb angle/LL: one parallel to top of a L1 vertebra, one parallel to a bottom of a L5 vertebra, and one line perpendicular to each of previous lines. An intersection of perpendicular lines is used to extract a Lumbar Lordosis Angle (LLA), which is smaller of two angles formed by intersection, typically in a range of 0°-30°.

Current methods for DHI measurement and LL angle measurement have wide variations which can result in continued sufferance for back pain patients, disability, and poor quality of life.

BRIEF DESCRIPTION OF THE DRAWINGS

At least one embodiment may be understood more fully from the detailed description given below and from accompanying drawings, which, however, should not be taken to limit the disclosure to the specific embodiment, but are for explanation and understanding.

FIG. 7 illustrates a flowchart of a method of calculating DHI, in accordance with at least one embodiment.

FIG. 10 illustrates images showing a process of segmentation of a disc, in accordance with at least one embodiment.

DETAILED DESCRIPTION

Figure 1:
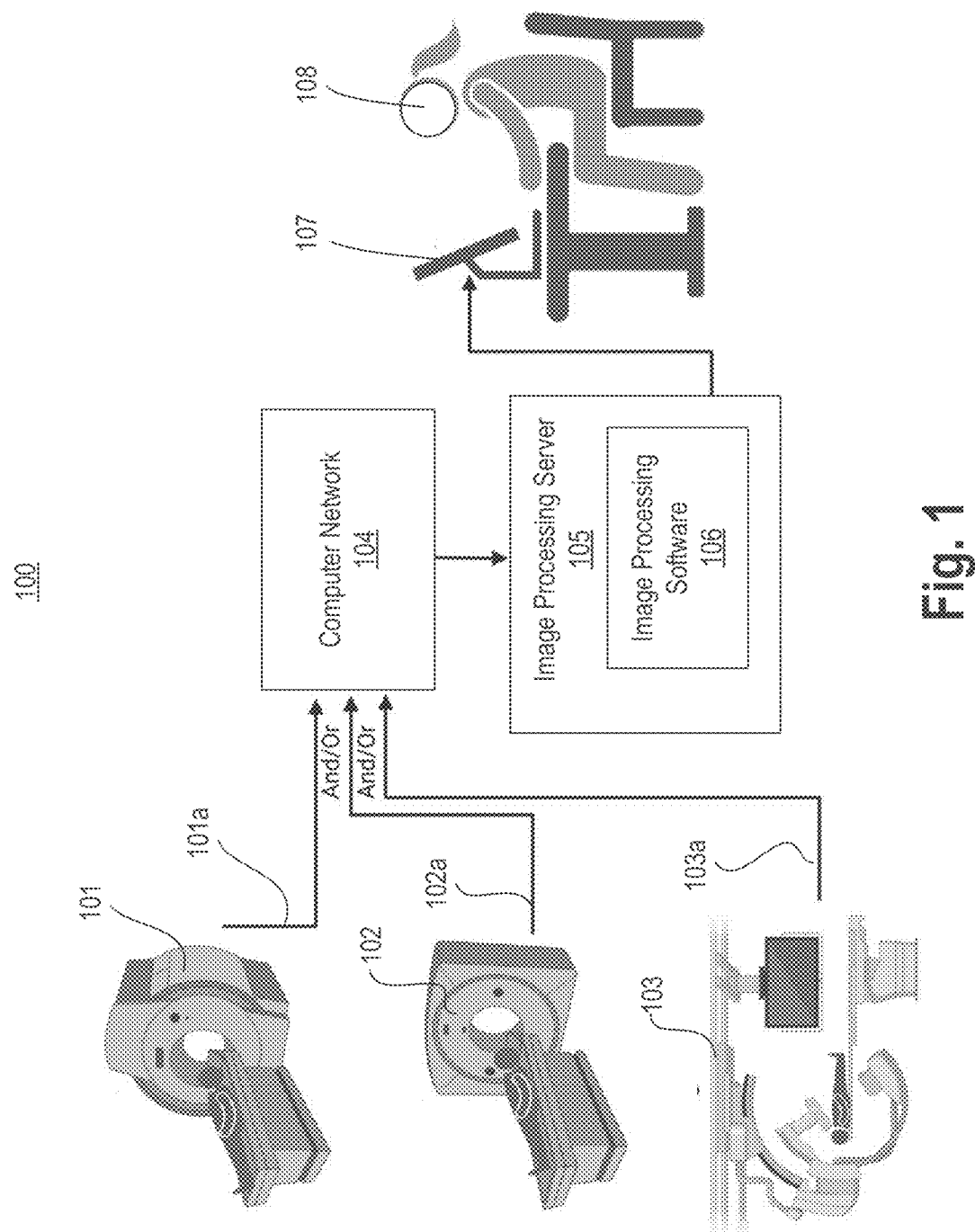
FIG. 1 illustrates a high-level block diagram of measuring lumber spine, in accordance with at least one embodiment.

When considering which spine surgery a patient is to receive, a physician may make measurements of one or more radiographs (X-ray, CT, or MRI) of the patient's spine. In low back, two common measurements are angle of curvature of lumbar region of spine, known as lumbar lordosis (LL), and height of disc relative to neighboring vertebrae, known as disc height index (DHI). LL may vary between healthy individuals. People with back pain may have a changed LL due to degeneration of intervertebral discs. A physician would measure LL for several reasons. LL may correlate with certain surgical complications or negative outcomes. A physician may use LL measurement to help determine if a patient is appropriate for a certain surgical procedure. A physician may measure LL to determine if it needs to be corrected as part of a surgery they are considering. They might also aim to maintain natural LL if performing a less invasive procedure. A physician may simply monitor this angle to determine disease progression. LL is most frequently measured using Cobb method, where a surgeon or radiologist may manually place a line, in an image, at an interface of a vertebral body and disc (endplate) on dorsal side of T12/L1 disc and caudal side of L5/S1 disc and reference angle of intersecting point. Endplates of normal discs are curved, and degeneration often leads to end plate defects that make them even less linear. Cobb method's reliance on placement of a straight line on a curved or wavy surface may lead to wide intra-observer and inter-observer variation in its measurement, making it not widely useful as a predictive metric of procedural fit.

DHI is a measure of how degenerated an individual disc is. Because taller individuals have taller discs, height of disc itself is not an indicator of disc health, but if this measurement is normalized to neighboring vertebrae, it may give an indication of whether a certain disc has degenerated and lost height. Like LL, DHI is a measurement to track disease progression. It has been shown to correlate with patient outcomes in certain procedures as well. Like LL, DHI relies on a user placing lines, in an image, at dorsal and caudal endplates of a disc as well as endplates of an adjunct vertebrae. Since endplates are curved or wavy, there is wide intra-observer and interobserver variation in this metric as well. To mitigate this variation, health industry relies on improved training and physicians and radiologists in line placement. However, this approach has significant flaws or drawbacks in that there is still little reliability in measurements.

At least one embodiment describes an alternative technique (e.g., apparatus and method) aimed at improving consistency of LL and DHI measurements. In at least one embodiment, rather than requiring an observer to visually estimate the location and orientation of disc boundaries, cross-sectional area and center of mass of segmented intervertebral discs (IVDs) in an image are used to determine dimensions and alignment of spinal structures. In at least one embodiment, segmented object (or segmented image) center of mass and axis orientation of IVDs may be used for calculating LL. In at least one embodiment, IVD pixel area and bounding box width may be used for calculating DHI.

At least one embodiment takes form of a software algorithm that takes inputs from hardware such as Magnetic Resonance Imaging (MRI), Computed Tomography (CT), or X-ray imaging machines. In at least one embodiment, these inputs (e.g., images) are then processed by a computer (e.g., one or more processors). In at least one embodiment, images from various machines (e.g., MRI, CT, x-Ray) are divided into segmented discs and these segmented discs are then processed to calculate DHI and LL.

In at least one embodiment, scheme for measuring DHI and LL angles result in consistent and more accurate results across a variety of health professionals. In at least one embodiment, an automated scheme may be used which reduces errors caused by manual measurement of DHI and LL angles.

At least one embodiment will be understood more fully from the detailed description given below and from the accompanying drawings, which, however, should not be taken to limit at least one embodiment, but are for explanation and understanding only.

Here, numerous details are discussed to provide a more thorough explanation of at least one embodiment. At least one embodiment may be practiced without these specific details by a person skilled in the art. In other instances, well-known structures and devices are shown in block diagram form, rather than in detail, to avoid obscuring at least one embodiment.

Note that in corresponding drawings of at least one embodiment, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary implementations to facilitate easier understanding of a circuit or a logical unit. Any represented signal, as dictated by design needs or preferences, may actually comprise one or more signals that may travel in either direction, and may be implemented with any suitable type of signal scheme.

It is pointed out that those elements of figures having same reference numbers (or names) as elements of any other figure can operate or function in any manner like that described but are not limited to such.

FIG. 1 illustrates a high-level block diagram 100 of measuring lumber spine, in accordance with at least one embodiment. In at least one embodiment, high-level block diagram 100 comprises Magnetic Resonance Imaging (MRI) machine 101, Computed Tomography (CT) machine 102, X-ray machine 103, computer network 104, image processing server 105, image processing software 106, display 107, and user or provider 108. In at least one embodiment, patient data from one or more of MRI machine 101, CT machine 102, and/or X-ray machine 103 are received by image processing server 105 via computer network 104. In at least one embodiment, computer network 104 can be wireless, wired, or a combination of them. In at least one embodiment, computer network 104 communicates with MRI machine 101, CT machine 102, and/or X-ray machine 103 via communication links 101a, 102a, and 103a, respectively. In at least one embodiment, communication links 101a, 102a, and 103a are wireless or wired links, or a combination of them. In at least one embodiment, X-ray imaging by X-ray imaging machine 103 can be performed either lying down or standing up. In at least one embodiment, image processing server 105 segments images from MRI machine 101, CT machine 102, and/or X-ray imaging machine 103 into segmented discs and these segmented discs are then processed to calculate DHI and LL. In at least one embodiment, image processing server 105 determines image segment center of mass and axis orientation of IVDs collected from one or more machines such as MRI machine 101, CT machine 102, and/or X-Ray machine 103. In at least one embodiment, image processing server 105 uses image segment center of mass and axis orientation of IVDs for calculating LL. In at least one embodiment, image processing server 105 uses IVD pixel area and bounding box width for calculating DHI. In at least one embodiment, output of image processing server 105 is exhibited on display 107, and this information is used by provider 108 to make an optimal decision for well-being of a patient.

Figure 2:
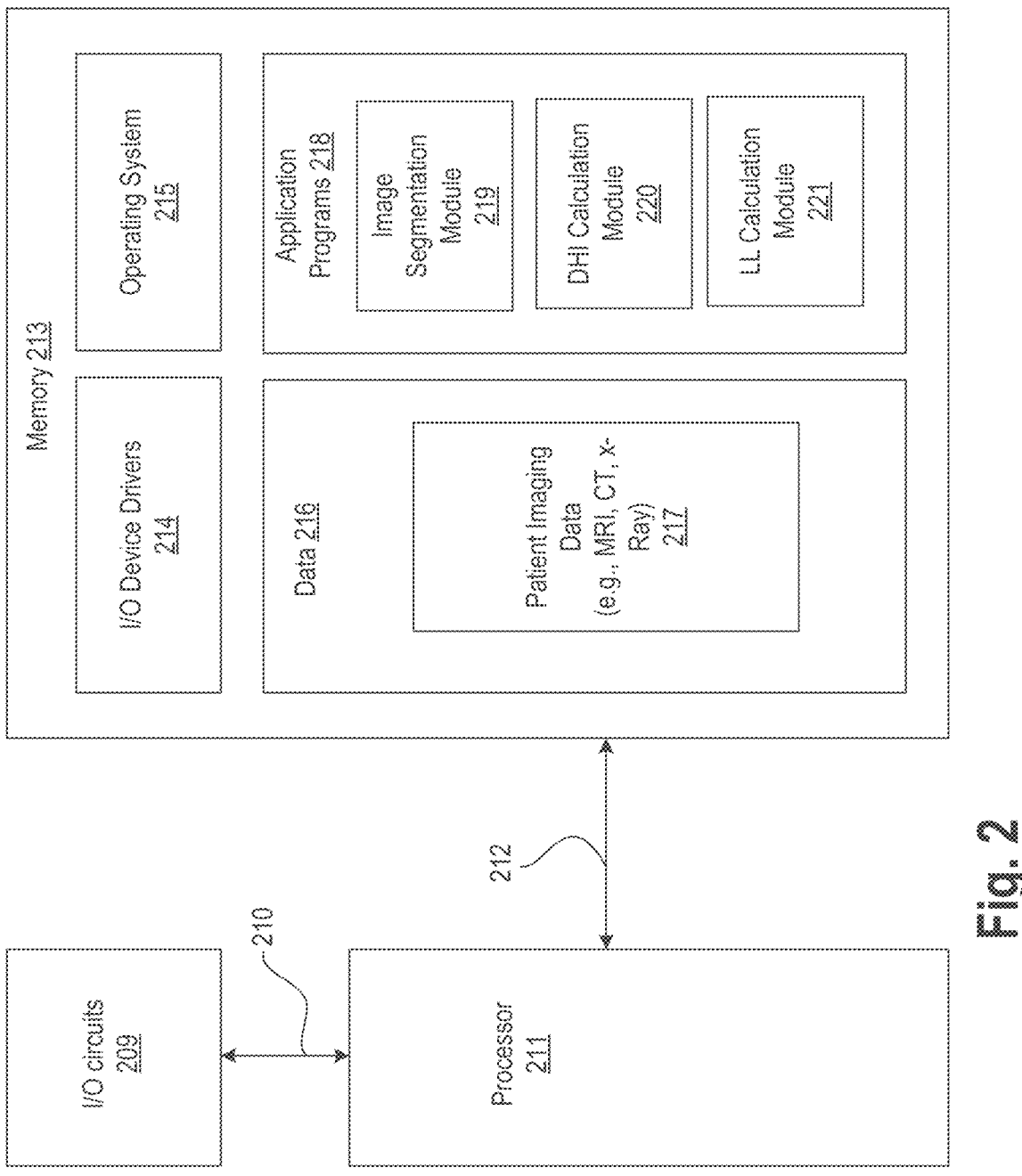
FIG. 2 illustrates an apparatus for measuring lumber spine, in accordance with at least one embodiment.

FIG. 2 illustrates apparatus 200 for measuring lumber spine, in accordance with at least one embodiment. In at least one embodiment, apparatus 200 illustrates details of image processing server 105. In at least one embodiment, apparatus 200 comprises input-output (I/O) circuits 209, interconnect 210, processor 211, interconnect 212, and memory 213 coupled as shown. In at least one embodiment, memory 213 includes I/O device drivers 214, operating system 215, storage area 216 to store data including patient imaging data 217 (e.g., MRI, CT, and/or X-ray), and application programs 218. In at least one embodiment, application programs 218 include an image segmentation module 219, a DHI calculation module 220, and LL calculation module 221.

In at least one embodiment, I/O circuits 209 may be any suitable I/Os that can receive data from computer network 104 and/or machines 101, 102, and/or 103. In at least one embodiment, examples of such I/Os are Peripheral Component Interconnect Express (PCIe), Serial Advanced Technology Attachment (SATA), and other serial or parallel interfaces. In at least one embodiment, interconnect 210 and interconnect 212 include any suitable interconnect for transmitting data to and from processor 211. In at least one embodiment, examples of such interconnect include double-data-rate (DDR) complaint interconnect, Universal serial bus (USB) complaint interconnect, etc. Processor 211 can be a Digital Signal Processor (DSP), an Application Specific Integrated Circuit (ASIC), a general-purpose Central Processing Unit (CPU), Graphics Processor Unit (GPU), or a low power logic implementing a simple finite state machine to perform the method of various embodiments, etc.

In at least one embodiment, memory 213 can include nonvolatile (state does not change if power to the memory device is interrupted) and/or volatile (state is indeterminate if power to the memory device is interrupted) memory devices. In at least one embodiment, examples of nonvolatile memory include flash memory, magnetic memory, resistive memory, ferroelectric memory, etc. In at least one embodiment, examples of volatile memory include static random-access memory, dynamic random-access memory, etc. In at least one embodiment, memory 213 can store application data, user data, documents, or other data, as well as system data (whether long-term or temporary) related to the execution of applications and functions of apparatus 200.

At least one embodiment is provided as a machine-readable medium (e.g., memory 213) for storing the computer-executable instructions (e.g., instructions to implement any other processes discussed herein). In at least one embodiment, machine-readable medium may include, but is not limited to, flash memory, optical disks, CD-ROMs, DVD ROMs, RAMs, EPROMs, EEPROMs, magnetic or optical cards, phase change memory (PCM), or other types of machine-readable media suitable for storing electronic or computer-executable instructions. At least one embodiment may be downloaded as a computer program (e.g., BIOS) which may be transferred from a remote computer (e.g., a server) to a requesting computer (e.g., a client) by way of data signals via a communication link (e.g., a modem or network connection).

In at least one embodiment, apparatus 200 includes connectivity that can include multiple different types of connectivity. In at least one embodiment, apparatus 200 may include cellular connectivity and wireless connectivity. In at least one embodiment, cellular connectivity refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. In at least one embodiment, wireless connectivity (or wireless interface) refers to wireless connectivity that is not cellular and can include personal area networks (such as Bluetooth, Near Field, etc.), local area networks (such as Wi-Fi), and/or wide area networks (such as LTE), or other wireless communication.

In at least one embodiment, image segmentation module 219 may be used to segment images from various machines such as MRI machine 101, CR machine 102, and/or X-ray machine 103 into segmented discs. In at least one embodiment, these segmented discs are processed to calculate DHI and LL. An example of this operation is visually illustrated in FIG. 5, in accordance with at least one embodiment. In at least one embodiment, DHI calculation module 220 may be used to calculate DHI. In at least one embodiment, DHI calculation module 220 may use IVD pixel area and bounding box width for calculating DHI. An example of this operation is visually illustrated in FIG. 3A, in accordance with at least one embodiment. In at least one embodiment, LL calculation module 221 and/or DHI calculating module 220 may determine image segment center of mass and axis orientation of IVDs collected from one or more machines such as MRI machine 101, CR machine 102, and/or X-ray machine 103. In at least one embodiment, LL calculation module 221 may use image center of mass and axis orientation of IVDs for calculating LL.

Figure 3A:
FIGS. 3A-B illustrate images of spine showing disc height index (DHI) calculation, and Lumbar Lordosis (LL) calculation, respectively, in accordance with at least one embodiment.
Figure 3B:
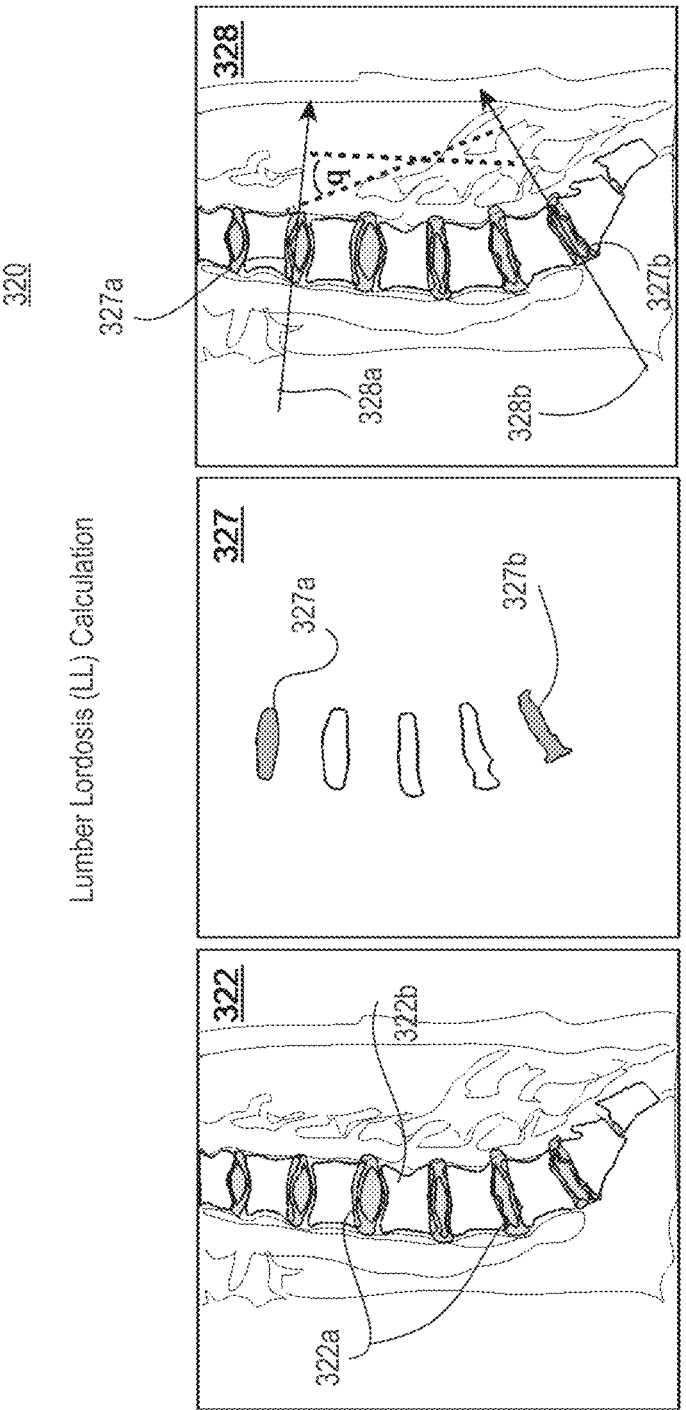

FIGS. 3A-B illustrates images 300 and 320 of spine showing disc height index (DHI) calculation, and Lumbar Lordosis (LL) calculation, respectively, in accordance with at least one embodiment. In at least one embodiment, image 322 may be a radiograph of a lumbar spine with discs 322a lumber vertebra 322b between discs 322a. In at least one embodiment, image 322 may be obtained from one or more machines such as MRI machine 101, CT machine 102, and/or X-ray machine 103. In at least one embodiment, image 323 is of segmented IVDs. Disc 323a may be selected as an example for DHI calculation, in at least one embodiment. In at least one embodiment, image 324 may be of a disc of interest (e.g., disc 323a) and this image is used for calculating centroid and orientation for disc and its caudal neighbor. In at least one embodiment, image 325 may be of rotation of both discs so that they are normal to a reading frame and for creating a bounding box around each disc. In at least one embodiment, image 325 may be used for calculating width of bounding box and a total area of segmented disc. In at least one embodiment, image 326 shows calculation of approximate disc height by dividing total disc area by width of bounding box.

In at least one embodiment, process of DHI and/or LL calculation further comprises finding a top edge of lower disc by finding a centroid location and taking half height as calculated above and finding point that is 0.5 times a disc height away from centroid normal to long axis of disc. In at least one embodiment, process of DHI and/or LL calculation further comprises finding length of distance between two points to approximate a vertebral body height. Here, a is a vertical distance between discs while β is disc height (e.g., disc area divided by boundary box width). In at least one embodiment, image 327 shows identification of top and bottom lumber IVDs as IVD 327a and IVD 327b. In at least one embodiment, image 328 shows finding orientation of upper and lower IVDs of lumbar spine, shown as IVD 327a and IVD 327b, and calculating their intersecting angle or intersecting angle of lines normal to them, which is same measurement. Here, dotted lines normal to lines 328a and 328b (that pass through center of IVD 327a and IVD 327b)

may be used to calculate interesting angle, in accordance with at least one embodiment.

Figure 4:
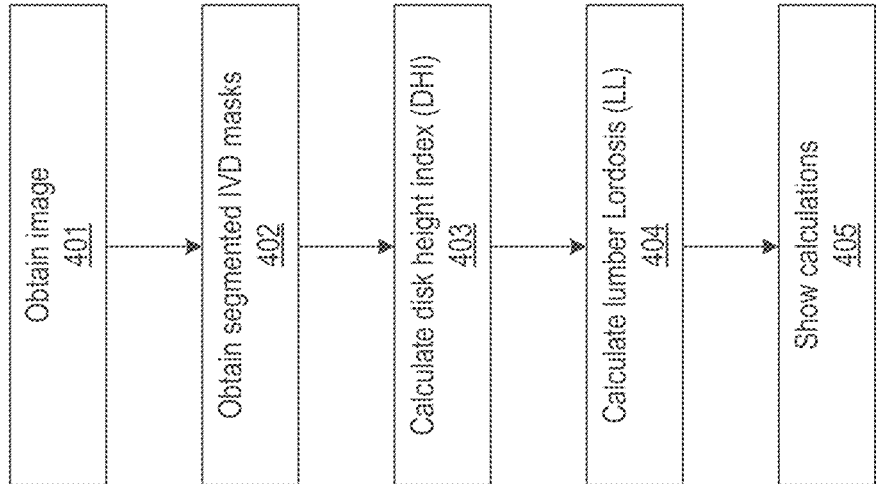
FIG. 4 illustrates a high-level flowchart of method for measuring lumber spine, in accordance with at least one embodiment.

FIG. 4 illustrates flowchart 400 of method for measuring lumber spine, in accordance with at least one embodiment. While various blocks here are shown in an order, order for some blocks may be modified. For example, in at least one embodiment, some blocks may be performed simultaneously or in parallel, and some blocks may be performed out of order. In at least one embodiment, various blocks can be performed by software, hardware, or a combination of them. Any suitable programming language can be used for implementing some or all blocks of flowchart 400.

At block 401, in at least one embodiment, an image (or one or more images) is obtained from a machine (e.g., a machine to perform radiography). In at least one embodiment, image segment center of mass and axis orientation of intervertebral discs (IVDs) is used to calculate lumbar lordosis (LL). At block 402, in at least one embodiment, segmented IVD masks are obtained. In at least one embodiment, a first disc and a second disc are identified from images of segmented IVDs. In at least one embodiment, a centroid and orientation for first disc and second disc are computed from images of segmented IVDs.

In at least one embodiment, instead of, or in addition to, calculating center of mass and orientations for IVDs, image processing software 106 may calculate center of mass and orientations for vertebral bodies. In at least one embodiment, image processing software 106 can determine vertebral body height based on total pixel area and a bounding box width. In at least one embodiment, image processing software 106 may then consider endplate a distance of half height away from centroid of vertebral body in a direction normal to long axis of orientation. In at least one embodiment, disc height can be considered as a distance between endplate lines for neighboring vertebral bodies.

In at least one embodiment, first pixel area of first disc may be computed. In at least one embodiment, first width of first disc may be computed. In at least one embodiment, a first disc height of first disc may be computed based on first pixel area and first width. In at least one embodiment, second pixel area of second disc may be computed. In at least one embodiment, a second width of second disc may be computed. In at least one embodiment, a second disc height of second disc may be computed based on second pixel area and second width.

In at least one embodiment, computing first disc height and second disc height comprises rotating first disc and second disc such that first disc and second disc are normal to a reading frame. In at least one embodiment, computing first disc height and second disc height comprises creating a first bounding box around first disc and a second bounding box around second disc in response to rotating first disc and second disc. In at least one embodiment, computing first pixel area comprises summing area of individual pixels in first disc. In at least one embodiment, computing second pixel area comprises summing area of individual pixels in second disc. In at least one embodiment, first width may be a width of first bounding box. In at least one embodiment, second width may be a width of second bounding box.

In at least one embodiment, computing first disc height and second disc height comprises calculating a first height of first disc based on first pixel area and first width. In at least one embodiment, computing first disc height and second disc height further comprises calculating a second height of second disc based on second pixel area and second width. In at least one embodiment, computing first disc height and second disc height comprises determining a first top edge of first disc prior to rotating first disc such that first disc in its original orientation. In at least one embodiment, determining first top edge comprises applying half of first height along a first short axis of original orientation of first disc. In at least one embodiment, computing first disc height and second disc height further comprises determining a second bottom edge of second disc prior to rotating second disc such that second disc in its original orientation. In at least one embodiment, determining second bottom edge comprises applying half of second height along a second short axis of original orientation of second disc.

In at least one embodiment, a first vertebral height may be computed. In at least one embodiment, computing first vertebral height comprises determining an approximate vertebral height by calculating a distance between a first point located at first top edge where it intersects with short axis of first disc and a second point extending from second bottom edge where it intersects with short axis of second disc. In at least one embodiment, first disc height index may be computed by dividing first disc height by approximate vertebral height to determine a disc height index.

In at least one embodiment, computing a centroid and orientation for a first disc and a second disc comprises determining a first centroid and a first orientation of first disc, wherein first disc is T12/L1 or L1/L2. In at least one embodiment, computing a centroid and orientation for a first disc and a second disc comprises determining a second centroid and a second orientation of second disc, wherein second disc may be T5/S1. In at least one embodiment, computing a centroid and orientation for a first disc and a second disc comprises computing an angle of lumbar lordosis (LL) based on first centroid and first orientation, and second centroid and second orientation.

At block 403, in at least one embodiment, DHI may be calculated. In at least one embodiment, IVD pixel area and bounding box width may be used to calculate DHI. In at least one embodiment, disc width may be more reliable than height given by bounding box due to endplate defects. In at least one embodiment, height may be approximated using total pixel area divided by width instead of utilizing bounding box height itself.

At block 404, in at least one embodiment, LL may be calculated. In at least one embodiment, image processing software 106 may calculate LL using orientation axes originating from centroid of vertebral body at L1 and L5.

At block 405, in at least one embodiment, calculations may be performed and line placement may be evaluated. In at least one embodiment, calculations and line placement are shown on a monitor or an interactive device. In at least one embodiment, apparatus and method described herein makes measurements for kyphosis using DHI calculation method, but in cervical or thoracic spine. Concepts of at least one embodiment can be adapted as a variety of products. In at least one embodiment, apparatus and method may be used to make a surgical decision support software to determine optimal procedure for a given back pain patient. In that case, at least one embodiment may be a part of creation of developing these predictive tools. Apparatus and method of at least one embodiment may be used by orthopedic medical device or imaging companies. Apparatus and method of at least one embodiment may be used to make diagnostic software for determining spine disease status and progression. In that case, apparatus, and method of at least one embodiment may be a part of creation of these diagnostic tools. Such tools may also be used by orthopedic medical devices or imaging companies.

Figure 5:
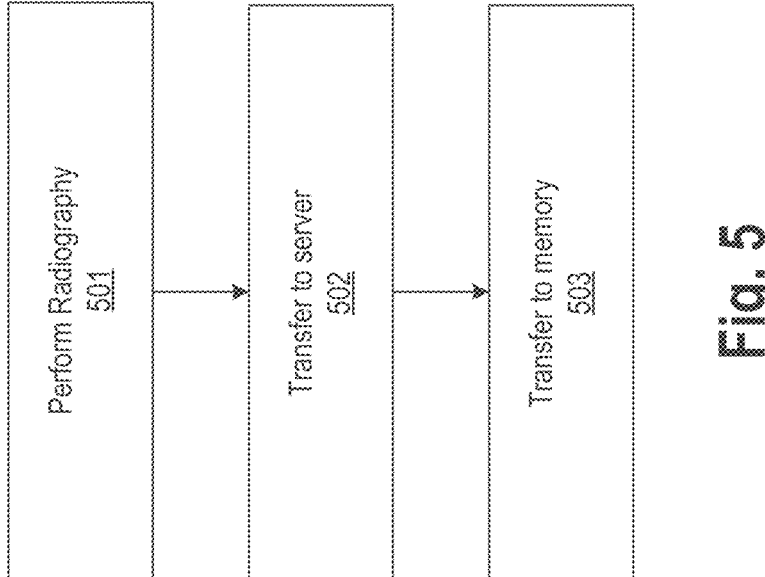
FIG. 5 illustrates a flowchart of a method of obtaining an image, in accordance with at least one embodiment.

FIG. 5 illustrates flowchart 500 of a method of obtaining an image (e.g., block 401 of flowchart 400), in accordance with at least one embodiment. While various blocks here are shown in order, order for some blocks may be modified. For example, in at least one embodiment, some blocks may be performed simultaneously or in parallel, and some blocks may be performed out of order. In at least one embodiment, various blocks can be performed by software, hardware, or a combination of them. Any suitable programming language can be used for implementing some or all blocks of flowchart 500. At block 501, in at least one embodiment, radiography may be performed. At block 502, in at least one embodiment, images obtained from radiography may be transferred to a server. At block 503, in at least one embodiment, images once received by a server are stored in memory.

Figure 6:
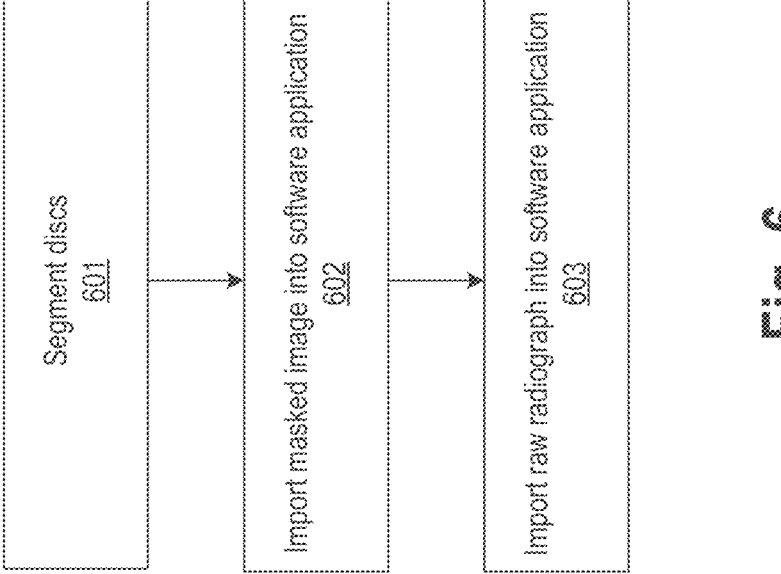
FIG. 6 illustrates a flowchart of a method of obtaining IVD masks, in accordance with at least one embodiment.

FIG. 6 illustrates a flowchart of a method of obtaining IVD masks (e.g., block 402), in accordance with at least one embodiment. While various blocks here are shown in order, order for some blocks may be modified. For example, in at least one embodiment, some blocks may be performed simultaneously or in parallel, and some blocks may be performed out of order. In at least one embodiment, various blocks can be performed by software, hardware, or a combination of them. Any suitable programming language can be used for implementing some or all blocks of flowchart 600. At block 601, in at least one embodiment, discs may be segmented. At block 602, in at least one embodiment, masked image is imported from memory. In at least one embodiment, masked image may be imported from memory into software application. In at least one embodiment, at block 603, raw radiograph image or data may be imported into software application.

FIG. 7 illustrates flowchart 700 of a method of calculating DHI (e.g., block 403), in accordance with at least one embodiment. While various blocks here are shown in order, order for some blocks may be modified. For example, in at least one embodiment, some blocks may be performed simultaneously or in parallel, and some blocks may be performed out of order. In at least one embodiment, various blocks can be performed by software, hardware, or a combination of them. Any suitable programming language can be used for implementing some or all blocks of flowchart 700. In at least one embodiment, at block 701, orientation and centroid of each IVD may be calculated. At block 702, in at least one embodiment, IVD may be rotated so orientation may be normal to reading frame. At block 703, in at least one embodiment, bounding box may be placed and width is calculated. At block 704, in at least one embodiment, IVD segmentation area may be calculated. At block 705, in at least one embodiment, height may be approximated by dividing IVD segmentation area calculated in block 704 with width calculated in block 703. At block 706, in at least one embodiment, top edge of IVD may be determined or identified in its original orientation using half of approximate height (e.g., 0.5×height from block 705) along short axis of orientation.

In at least one embodiment, at block 707, operations described with reference to block 701 through block 706 for one disc caudal are repeated for disc of interest. At block 708, in at least one embodiment, approximate vertebral height may be approximated by calculating a distance between lines identified in block 706 and block 707 at a point where they intersect with short axis of each disc orientation vectors. At block 709, in at least one embodiment, DHI may be calculated by dividing disc height (from block 705) with vertebral height (from block 708).

Figure 8:
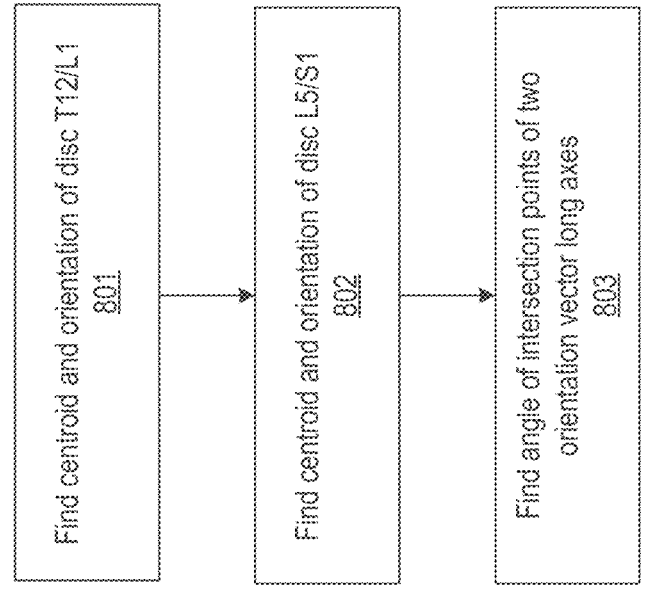
FIG. 8 illustrates a flowchart of a method of calculating LL, in accordance with at least one embodiment.

FIG. 8 illustrates flowchart 800 of a method of calculating LL (e.g., block 404), in accordance with at least one embodiment. While various blocks here are shown in order, order for some blocks may be modified. For example, in at least one embodiment, some blocks may be performed simultaneously or in parallel, and some blocks may be performed out of order. In at least one embodiment, various blocks can be performed by software, hardware, or a combination of them. Any suitable programming language can be used for implementing some or all blocks of flowchart 800. At block 801, in at least one embodiment, centroid and orientation of disc T12/L1 may be identified. At block 802, in at least one embodiment, centroid and orientation of disc L5/S1 may be identified. At block 803, in at least one embodiment, angle of intersection points of orientations from block 801 and block 802 may be determined (e.g., angle of intersection points of two orientation vector long axes is determined).

Figure 9:
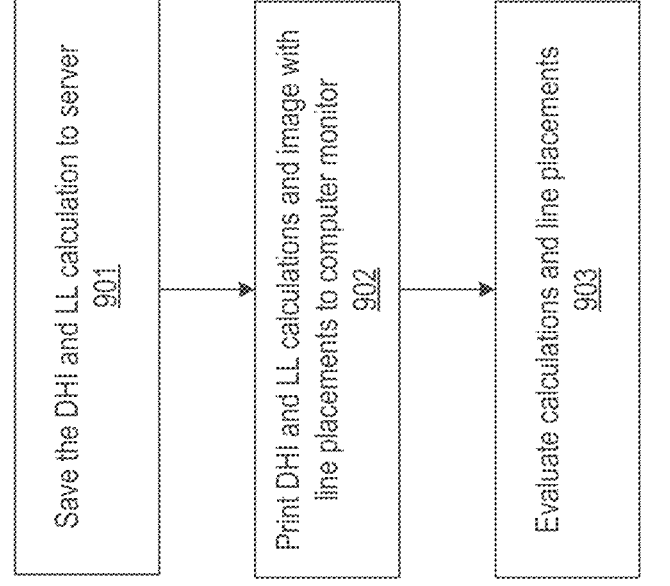
FIG. 9 illustrates a flowchart of a method of showing calculation, in accordance with at least one embodiment.

FIG. 9 illustrates a flowchart of a method of showing calculation, in accordance with at least one embodiment. While various blocks here are shown in order, order for some blocks may be modified. For example, in at least one embodiment, some blocks may be performed simultaneously or in parallel, and some blocks may be performed out of order. In at least one embodiment, various blocks can be performed by software, hardware, or a combination of them. Any suitable programming language can be used for implementing some or all blocks of flowchart 900. At block 901, in at least one embodiment, DHI and LL calculations may be saved to a server. In at least one embodiment, DHI and LL calculations may be saved in memory 213. In at least one embodiment, at block 902, DHI and LL calculations and image with line placements may be printed or displayed to a monitor (e.g., computer monitor). In at least one embodiment, at block 903, DHI and LL calculations may be evaluated. In at least one embodiment, a physician, a radiologist, or a medical expert may evaluate DHI and LL calculations and line placements.

FIG. 10 illustrates a set of images 1000 showing process of segmentation of a disc, in accordance with at least one embodiment. In at least one embodiment, image 1020 shows a boundary generated around an IVD (e.g., IVD 327*a* or IVD 327*b*). In at least one embodiment, edges of boundary are determined as indicated by points 1001, 1002, 1003, 1004, 1005, 1006, 1007, 1008, 1009, 1010, 1011, and 1012. Fewer or more points can be identified, in at least one embodiment. In at least one embodiment, one or more image processing techniques may be used to determine points that indicate abrupt edges of a boundary. In at least one embodiment, lines connecting points result in a bounding area of an IVD.

Figure 11:
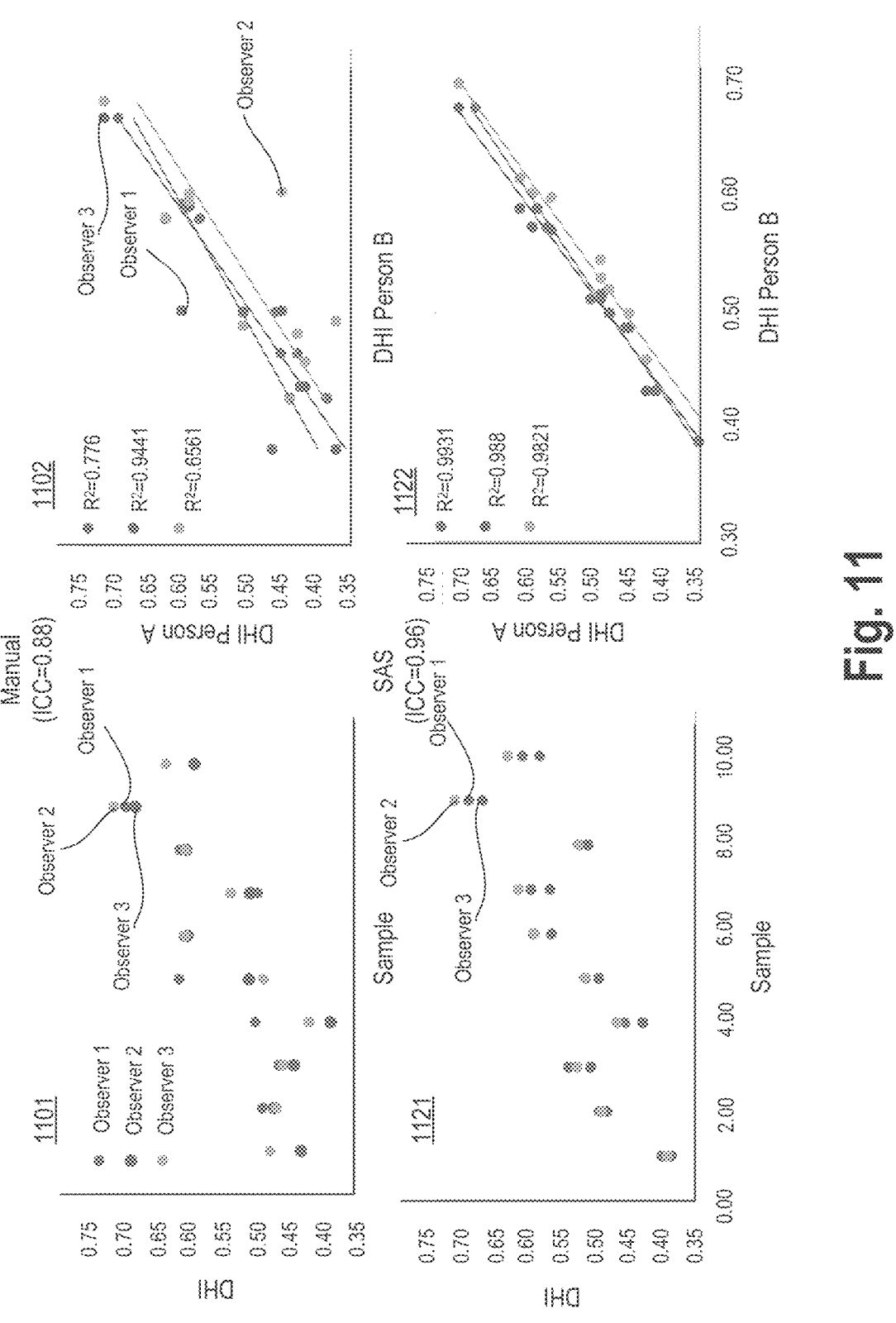
FIG. 11 illustrates a set of plots showing comparison of disc height index interobserver variability using traditional method and method discussed herein, in accordance with at least one embodiment.

FIG. 11 illustrates a set of plots 1101, 1102, 1121, and 1122 showing comparison of disc height index interobserver variability using traditional method and method discussed herein, in accordance with at least one embodiment. In at least one embodiment, two images on top row (e.g., plots 1101 and 1102) show data that is manually generated by three observers (observer 1, observer 2, and observer 3) to measure DHI using traditional method. In at least one embodiment, two images on bottom row (e.g., plots 1121 and 1122) show data that is generated by three observers (observer 1, observer 2, and observer 3) to measure DHI using method of at least one embodiment. Clearly, DHI for person A relative to DHI generated by person B is consistently of high accuracy and less variability using method of at least one embodiment. In this case, three dots are shown per sample for method of at least one embodiment because each observer determines a slightly different segmentation area. In at least one embodiment, upon automating process of determining segmentation area of disc, sample points land on top of one another.

Figure 12:
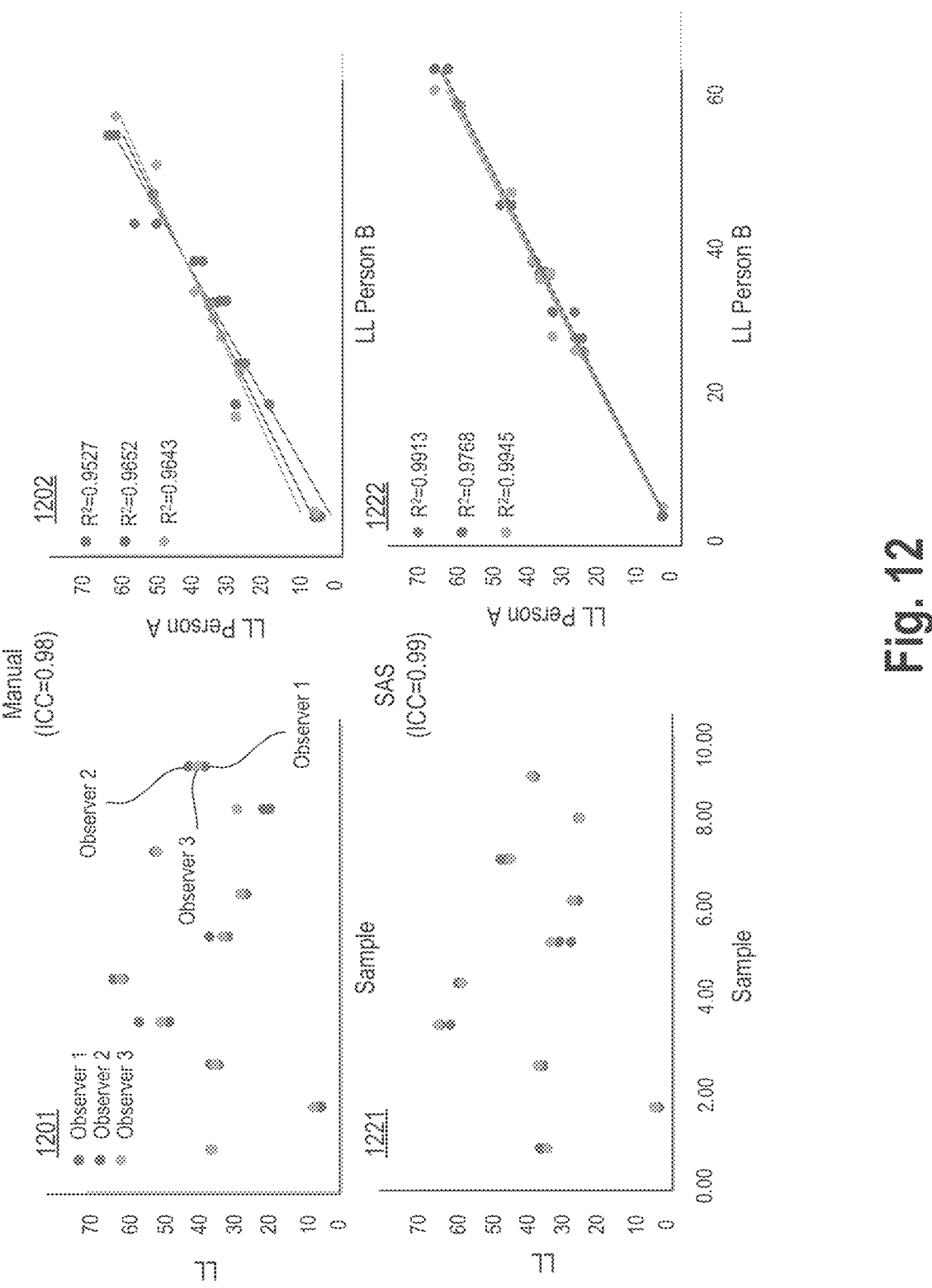
FIG. 12 illustrates a set of plots showing comparison of lumbar lordosis index interobserver variability using traditional method of and the method discussed herein, in accordance with at least one embodiment.

FIG. 12 illustrates a set of plots 1201, 1202, 1221, and 1222 showing comparison of lumbar lordosis index inter-observer variability using traditional method of and method discussed herein, in accordance with at least one embodiment. In at least one embodiment, two images on top row (e.g., plots 1201 and 1202) show data that is manually generated by three observers (observer 1, observer 2, and observer 3) to measure LL using traditional method. Two images on bottom row (e.g., plots 1221 and 1222) show data that is generated by three observers (observer 1, observer 2, and observer 3) to measure LL using methods of various embodiments. In at least one embodiment, LL for person A relative to LL generated by person B is consistently of high accuracy and less variability using method of various embodiments. In this case, three dots are shown per sample for method of at least one embodiment because each observer determines a slightly different segmentation area. In at least one embodiment, upon automating process of determining segmentation area of disc, sample points land on top of one another.

Here, "connected" herein generally refers to a direct connection, such as electrical, mechanical, or magnetic connection between things that are connected, without any intermediary devices.

Here, "coupled" may generally refer to a direct or indirect connection, such as a direct electrical, mechanical, or magnetic connection between things that are connected or an indirect connection, through one or more passive or active intermediary devices.

Here, "adjacent" may generally refer to a position of a thing being next to (e.g., immediately next to or close to with one or more things between them) or adjoining another thing (e.g., abutting it).

Here, "circuit" or "module" may generally refer to one or more passive and/or active components or software code that are arranged to cooperate with one another to provide a desired function.

Here, "signal" may refer to at least one current signal, voltage signal, magnetic signal, or data/clock signal. Here, meaning of "a," "an," and "the" include plural references. Here, meaning of "in" includes "in" and "on."

Here, "substantially," "close," "approximately," "near," and "about," may generally refer to being within +/−10% of a target value.

Unless otherwise specified, use of ordinal adjectives "first," "second," and "third," etc., to describe a common object, merely indicate that different instances of like objects are being referred to and are not intended to imply that objects so described must be in a given sequence, either temporally, spatially, in ranking or in any other manner.

For purposes of present disclosure, phrases "A and/or B" and "A or B" mean (A), (B), or (A and B). For purposes of present disclosure, phrase "A, B, and/or C" means (A), (B), (C), (A and B), (A and C), (B and C), or (A, B and C).

Here, "left," "right," "front," "back," "top," "bottom," "over," "under," and like in are used for descriptive purposes and not necessarily for describing permanent relative positions.

Reference in the specification to "an embodiment," "one embodiment," "some embodiments," "at least one embodiment," or "other embodiments" means that a particular feature, structure, or characteristic described in connection with the embodiments is included in at least one embodiment and not all embodiments. Here, various appearances of "an embodiment," "one embodiment," "at least one embodiment," or "some embodiments" are not necessarily all referring to the same embodiments. If at least one embodiment states a component, feature, structure, or characteristic "may," "might," or "could" be included, that particular component, feature, structure, or characteristic is not required to be included. If at least one embodiment or claim refers to "a" or "an" element, that does not mean there is only one of the elements. If at least one embodiment or claim refers to "an additional" element, that does not preclude there being more than one of the additional elements.

Furthermore, the particular features, structures, functions, or characteristics may be combined in any suitable manner in one or more embodiments. For example, a first embodiment may be combined with a second embodiment anywhere the particular features, structures, functions, or characteristics associated with the two embodiments are not mutually exclusive.

While disclosure has been described in conjunction with at least one embodiment thereof, many alternatives, modifications, and variations of such at least one embodiment may be apparent to those of ordinary skill in art considering foregoing description. At least one embodiment is intended to embrace all such alternatives, modifications, and variations as to fall within broad scope of appended claims. Where specific details are set forth to describe at least one embodiment, it should be apparent to one skilled in art that disclosure can be practiced without, or with variation of, these specific details. Description is thus to be regarded as illustrative instead of limiting.

In at least one embodiment, structures described herein can also be described as method(s) of forming those structures or apparatuses, and method(s) of operation of these structures or apparatuses. Following examples are provided that illustrate at least one embodiment. An example can be combined with any other example. As such, at least one embodiment can be combined with at least another embodiment without changing scope of an embodiment.

Example 1: A method comprising: receiving images of segmented intervertebral discs (IVDs); identifying a first disc and a second disc from the images of the segmented IVDs, wherein the second disc is a caudal neighbor of the first disc; and computing a centroid and orientation for the first disc and the second disc from the images of segmented IVDs.

Example 2: The method of example 1 comprising: computing a first pixel area of the first disc; computing a first width of the first disc; and computing a first disc height of the first disc based on the first pixel area and the first width.

Example 3: The method of example 2 comprising: computing a second pixel area of the second disc; computing a second width of the second disc; and computing a second disc height of the second disc based on the second pixel area and the second width.

Example 4: The method of example 3, wherein computing the first disc height and the second disc height comprises rotating the first disc and the second disc such that the first disc and the second disc are normal to a reading frame.

Example 5: The method of example 4, wherein computing the first disc height and the second disc height comprises creating a first bounding box around the first disc and a second bounding box around the second disc in response to rotating the first disc and the second disc.

Example 6: The method of example 5, wherein computing the first pixel area comprises summing area of first individual pixels in the first disc, and wherein computing the second pixel area comprises summing area of second individual pixels in the second disc.

Example 7: The method of example 5, wherein the first width is a width of the first bounding box, wherein the second width is a width of the second bounding box.

Example 8: The method of example 6, wherein computing the first disc height and the second disc height comprises: calculating a first height of the first disc based on the first pixel area and the first width; and calculating a second height of the second disc based on the second pixel area and the second width.

Example 9: The method of example 8, wherein computing the first disc height and the second disc height comprises: determining a first top edge of the first disc prior to rotating the first disc such that the first disc is an original orientation, wherein determining the first top edge comprises applying a half of the first height along a first short axis of the original orientation of the first disc; and determining a second bottom edge of the second disc prior to rotating the second disc such that the second disc in its original orientation, wherein determining the second bottom edge comprises applying a half of the second height along a second short axis of the original orientation of the second disc.

Example 10: The method of example 9, comprising computing a first vertebral height, wherein computing the first vertebral height comprises determining an approximate vertebral height by calculating a distance between a first point located at the first top edge where it intersects with the first short axis of the first disc and a second point extending from the second bottom edge where it intersects with the second short axis of the second disc.

Example 11: The method of example 10, comprises computing a first disc height index by dividing the first disc height by the approximate vertebral height to determine a disc height index.

Example 12: The method of example 1, wherein computing the centroid and the orientation for the first disc and the second disc comprises: determining a first centroid and a first orientation of the first disc, wherein the first disc is T12/L1; determining a second centroid and a second orientation of the second disc, wherein the second disc is T5/S1; and computing an angle of lumbar lordosis based on the first centroid and the first orientation, and the second centroid and the second orientation.

Example 13: An apparatus comprising: one or more processors to measure lumber spine based, at least in part, on cross-sectional area and center of mass of segmented intervertebral discs (IVDs).

Example 14: The apparatus of example 13, wherein the one or more processors applies an image center of the mass and an axis orientation of segmented IVDs to calculate Lumbar Lordosis.

Example 15: The apparatus of example 13, wherein the one or more processors are to: receive images of the segmented IVDs; identify a first disc and a second disc from the images of the segmented IVDs, wherein the second disc is a caudal neighbor of the first disc; and compute a centroid and orientation for the first disc and the second disc from the images of the segmented IVDs.

Example 16: The apparatus of example 15, wherein the one or more processors are to: compute a first pixel area of the first disc; compute a first width of the first disc;

and compute a first disc height of the first disc based on the first pixel area and the first width.

Example 17: The apparatus of example 16, wherein the one or more processors are to: compute a second pixel area of the second disc; compute a second width of the second disc; and compute a second disc height of the second disc based on the second pixel area and the second width.

Example 18: The apparatus of example 17, wherein the one or more processors are to compute the first disc height and the second disc height by rotation of the first disc and the second disc such that the first disc and the second disc are normal to a reading frame.

Example 19: The apparatus of example 18, wherein the one or more processors are to compute the first disc height and the second disc height by creation of a first bounding box around the first disc and a second bounding box around the second disc in response to rotating the first disc and the second disc.

Example 20: A system comprising: one or more memories; and one or more processors coupled to the one or more memories, wherein the one or more processors are to: receive images of segmented intervertebral discs (IVDs); identify a first disc and a second disc from the images of the segmented IVDs, wherein the second disc is a caudal neighbor of the first disc; and compute a centroid and an orientation for the first disc and the second disc from the images of segmented IVDs.

An abstract is provided that will allow a reader to ascertain nature and gist of technical disclosure. Abstract is submitted with an understanding that it will not be used to limit scope or meaning of claims. Following claims are hereby incorporated into the detailed description, with each claim standing on its own as a separate embodiment.

We claim:

1. A method comprising:

receiving images of segmented intervertebral discs (IVDs) from image segmentation circuitry comprising neural network architecture configured to apply filters for feature extraction and classification to automatically segment intervertebral disc regions from medical imaging data;

identifying a first disc and a second disc from the images of the segmented IVDs, wherein the second disc is a caudal neighbor of the first disc;

computing a centroid and orientation for the first disc and the second disc from the images of segmented IVDs;

computing a first pixel width of the first disc;

computing a first disc height of the first disc based on pixel area and the first width by calculating the first disc height as pixel area divided by the first width;

computing a second width of the second disc; computing a second disc height of the second disc based on the pixel area and the second width by calculating the second disc height as the pixel area divided by the second width, wherein computing the first disc height and the second disc height comprises rotating the first disc and the second disc such that the first disc and the second disc are normal to a reading frame, and creating a first bounding box around the first disc; and a second bounding box around the second disc in response to rotating the first disc and the second disc, and wherein the first width is a width of the first bounding box and the second width is a width of the second bounding box; and generating, by report generation circuitry, a clinical diagnostic report containing the first disc height, second disc height, and comparison to normative data for display to healthcare providers.

2. The method of claim 1, wherein computing the first disc height and the second disc height comprises:

determining a first top edge of the first disc prior to rotating the first disc such that the first disc is an original orientation, wherein determining the first top edge comprises applying a half of the first disc height along a first short axis of the original orientation of the first disc; and determining a second bottom edge of the second disc prior to rotating the second disc such that the second disc in its original orientation, wherein determining the second bottom edge comprises applying a half of the second disc height along a second short axis of the original orientation of the second disc.

3. The method of claim 2, comprising computing a first vertebral height, wherein computing the first vertebral height comprises determining an approximate vertebral height by calculating a distance between a first point located at the first top edge where it intersects with the first short axis of the first disc and a second point extending from the second bottom edge where it intersects with the second short axis of the second disc.

4. The method of claim 3, comprises computing a first disc height index by dividing the first disc height by the approximate vertebral height to determine a disc height index.

5. The method of claim 1, wherein computing the centroid and the orientation for the first disc and the second disc comprises:

determining a first centroid and a first orientation of the first disc, wherein the first disc is T12/L1 or L1/L2;

determining a second centroid and a second orientation of the second disc, wherein the second disc is T5/S1; and computing an angle of lumbar lordosis based on the first centroid and the first orientation, and the second centroid and the second orientation.

6. An apparatus comprising:

image segmentation circuitry comprising neural network architecture configured to apply filters for feature extraction and classification to generate segmented intervertebral discs (IVDs);

one or more processors to measure lumbar spine based, at least in part, on cross-sectional area and center of mass of the segmented IVDs, wherein the image segmentation circuitry provides the segmented IVDs to the one or more processors, and wherein the one or more processors are to: compute a first width of a first disc;

compute a first disc height of the first disc based on pixel area and the first width by calculating the first disc height as pixel area divided by the first width;

compute a second width of a second disc; compute a second disc height of the second disc based on pixel area and the second width by calculating the second disc height as pixel area divided by the second width, wherein the one or more processors are to compute the first disc height and the second disc height by rotation of the first disc and the second disc such that the first disc and the second disc are normal to a reading frame, and by creation of a first bounding box around the first disc and a second bounding box around the second disc in response to rotating the first disc and the second disc;

report generation circuitry configured to receive the computed measurements from the one or more processors and generate clinical diagnostic reports containing disc measurements and comparisons to normative data; and display circuitry configured to present the clinical diagnostic reports to healthcare providers.

7. The apparatus of claim 6, wherein the one or more processors applies an image center of the mass and an axis orientation of segmented IVDs to calculate Lumbar Lordosis.

8. The apparatus of claim 6, wherein the one or more processors are to:

receive images of the segmented IVDs;

identify a first disc and a second disc from the images of the segmented IVDs, wherein the second disc is a caudal neighbor of the first disc; and compute a centroid and orientation for the first disc and the second disc from the images of the segmented IVDs.

9. A system comprising:

image segmentation circuitry comprising neural network architecture configured to generate segmented intervertebral discs (IVDs) by applying filters for feature extraction and classification to medical imaging data;

one or more memories; and one or more processors coupled to the one or more memories and the image segmentation circuitry, wherein the image segmentation circuitry receives the medical imaging data and generates the segmented IVDs using the neural network architecture, and wherein the one or more processors are to:

receive images of the segmented IVDs from the image segmentation circuitry;

identify a first disc and a second disc from the images of the segmented IVDs, wherein the second disc is a caudal neighbor of the first disc;

compute a centroid and an orientation for the first disc and the second disc from the images of segmented IVDs;

compute a first width of the first disc; compute a first disc height of the first disc based on pixel area and the first width by calculating the first disc height as pixel area divided by the first width;

compute a second width of the second disc;

compute a second disc height of the second disc based on pixel area and the second width by calculating the second disc height as pixel area divided by the second width, wherein the one or more processors are to compute the first disc height and the second disc height by rotation of the first disc and the second disc such that the first disc and the second disc are normal to a reading frame, and by creation of a first bounding box around the first disc and a second bounding box around the second disc in response to rotating the first disc and the second disc, and wherein the first width is a width of the first bounding box and the second width is a width of the second bounding box;

report generation circuitry configured to receive computed measurements from the one or more processors and generate clinical diagnostic reports with disc measurements and normative comparisons; and display circuitry configured to receive the clinical diagnostic reports and present annotated images with measurements to clinicians.

* * * * *